US012806399B2

(12) United States Patent
Thomas et al.

(10) Patent No.: US 12,806,399 B2
(45) Date of Patent: Nov. 24, 2026

(54) FLUID CONNECTOR FOR VASCULAR ACCESS DEVICE

(71) Applicant: Bard Peripheral Vascular, Inc., Franklin Lakes, NJ (US)

(72) Inventors: Ian N. Thomas, West Bountiful, UT (US); Brenda L. F. Fedor, Holladay, UT (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 907 days.

(21) Appl. No.: 18/021,153

(22) PCT Filed: Aug. 12, 2021

(86) PCT No.: PCT/US2021/045743
§ 371 (c)(1),
(2) Date: Feb. 13, 2023

(87) PCT Pub. No.: WO2022/036095
PCT Pub. Date: Feb. 17, 2022

(65) Prior Publication Data

US 2023/0321423 A1 Oct. 12, 2023

Related U.S. Application Data

(60) Provisional application No. 63/066,003, filed on Aug. 14, 2020.

(51) Int. Cl.
*A61M 39/12* (2006.01)

(52) U.S. Cl.
CPC .................................. *A61M 39/12* (2013.01)

(58) Field of Classification Search
CPC .. A61M 39/12; A61M 39/10; A61M 39/1011; A61M 39/02; A61M 39/0208;
(Continued)

(56) References Cited

U.S. PATENT DOCUMENTS 4,645,494 A 2/1987 Lee et al.
4,673,394 A 6/1987 Fenton, Jr. et al.
(Continued)

FOREIGN PATENT DOCUMENTS

CN 111765309 A 10/2020
EP 1986717 A2 11/2008
(Continued)

OTHER PUBLICATIONS

PCT/US2021/045743 filed Aug. 12, 2021 International Search Report and Written Opinion dated Jan. 11, 2022.
(Continued)

*Primary Examiner* — Kevin C Sirmons
*Assistant Examiner* — Alexandra Lalonde
(74) *Attorney, Agent, or Firm* — Rutan & Tucker LLP

(57) ABSTRACT

A coupling system is configured to couple a catheter to a port. The coupling system can include a toothed grip connector system configured to retain a portion of an end portion of the catheter. The toothed grip connector system can include a recess extending longitudinally from a first end of the coupling system and including an internal stem with a gripping member extending radially about the internal stem. The gripping member can include a plurality of teeth extending radially inward, the plurality of teeth configured to engage an outer surface of the end portion of the catheter to prevent longitudinal movement in at least a first direction following insertion of the end portion of the catheter into the recess. A sealing member can be included to provide a seal between the end portion of the catheter and the internal stem.

7 Claims, 11 Drawing Sheets

(58) Field of Classification Search

CPC .. A61M 2039/1016; A61M 2039/1027; A61M 2039/1072; A61M 2039/0202; A61M 2039/0205; A61M 2039/0229; A61M 2039/027; A61M 2039/0276; A61M 2039/0282; A61M 2039/1066

See application file for complete search history.

(56) References Cited

U.S. PATENT DOCUMENTS

| | | | |
|---|---|---|---|
| 4,704,103 | A | 11/1987 | Stober et al. |
| 4,720,285 | A | 1/1988 | Pickhard |
| 4,723,948 | A | 2/1988 | Clark et al. |
| 4,929,236 | A | 5/1990 | Sampson |
| 5,129,891 | A | 7/1992 | Young |
| 5,195,978 | A | 3/1993 | Schiffer |
| 5,312,337 | A | 5/1994 | Flaherty et al. |
| 5,632,729 | A | 5/1997 | Cai et al. |
| 5,637,102 | A | 6/1997 | Tolkoff et al. |
| 5,702,374 | A | 12/1997 | Johnson |
| 5,743,873 | A | 4/1998 | Cai et al. |
| 6,003,906 | A | 12/1999 | Fogarty et al. |
| 6,113,572 | A | 9/2000 | Gailey et al. |
| 6,453,185 | B1 | 9/2002 | O'Keefe |
| 6,582,401 | B1 | 6/2003 | Windheuser et al. |
| 6,592,544 | B1 | 7/2003 | Mooney et al. |
| 7,182,771 | B1 | 2/2007 | Houser et al. |
| 7,273,235 | B2 | 9/2007 | Coquard et al. |
| 7,452,354 | B2 | 11/2008 | Bright et al. |
| 7,637,893 | B2 | 12/2009 | Christensen et al. |
| 8,152,791 | B2 | 4/2012 | Goode et al. |
| 8,480,560 | B2 | 7/2013 | Vendely |
| 8,608,727 | B2 | 12/2013 | Michels et al. |
| 8,696,647 | B2 | 4/2014 | Bizup et al. |
| 8,936,582 | B2 | 1/2015 | Szweda et al. |
| 9,358,378 | B2 | 6/2016 | Hanson et al. |
| 9,427,553 | B2 | 8/2016 | Nelson |
| 10,139,025 | B2 | 11/2018 | Blake et al. |
| RE47,154 | E | 12/2018 | Porter et al. |
| 10,272,236 | B2 | 4/2019 | Davey |
| 10,584,818 | B2 | 3/2020 | Blake et al. |
| 10,627,030 | B2 | 4/2020 | Lewis et al. |
| 2002/0010425 | A1 | 1/2002 | Guo et al. |
| 2005/0173922 | A1 | 8/2005 | Coquard et al. |
| 2007/0016166 | A1 | 1/2007 | Thistle |
| 2007/0142709 | A1 | 6/2007 | Martone et al. |
| 2008/0009832 | A1 | 1/2008 | Barron et al. |
| 2008/0108969 | A1 | 5/2008 | Kerr |
| 2008/0114308 | A1 | 5/2008 | di Palma et al. |
| 2008/0214991 | A1 | 9/2008 | Haarala et al. |
| 2009/0112187 | A1 | 4/2009 | Goode et al. |
| 2009/0187158 | A1 | 7/2009 | Richmond |
| 2010/0121218 | A1 | 5/2010 | Mugan et al. |
| 2012/0109068 | A1 | 5/2012 | Vendely |
| 2015/0159066 | A1 | 6/2015 | Hartwell et al. |
| 2016/0106966 | A1* | 4/2016 | Jochum ............ A61M 39/0208 604/288.01 |
| 2016/0178101 | A1* | 6/2016 | Blake .................... F16L 33/225 29/428 |
| 2018/0193631 | A1 | 7/2018 | Hall et al. |
| 2019/0022368 | A1 | 1/2019 | Hall et al. |
| 2019/0224450 | A1 | 7/2019 | Arnar et al. |
| 2019/0232035 | A1 | 8/2019 | Fedor et al. |
| 2019/0336688 | A1 | 11/2019 | Bosshardt et al. |
| 2020/0108242 | A1 | 4/2020 | Stankowski et al. |
| 2021/0080043 | A1 | 3/2021 | Blake et al. |
| 2021/0247008 | A1 | 8/2021 | Sillitoe et al. |
| 2023/0277832 | A1 | 9/2023 | Hale |
| 2023/0405295 | A1 | 12/2023 | Fedor et al. |
| 2024/0316328 | A1 | 9/2024 | Andersen et al. |
| 2024/0358987 | A1 | 10/2024 | Andersen et al. |
| 2024/0424262 | A1 | 12/2024 | Andersen et al. |

FOREIGN PATENT DOCUMENTS

| | | | |
|---|---|---|---|
| KR | 20190106037 | A | 9/2019 |
| WO | 2005089851 | A1 | 9/2005 |
| WO | 2007081749 | A2 | 7/2007 |
| WO | 2016176065 | A1 | 11/2016 |
| WO | 2017027885 | A1 | 2/2017 |
| WO | 2019040801 | A1 | 2/2019 |
| WO | 2020052940 | A1 | 3/2020 |
| WO | 2022036095 | A1 | 2/2022 |
| WO | 2022108597 | A1 | 5/2022 |
| WO | 2023282899 | A1 | 1/2023 |
| WO | 2023033821 | A1 | 3/2023 |
| WO | 2023038632 | A1 | 3/2023 |
| WO | 2025042393 | A1 | 2/2025 |

OTHER PUBLICATIONS

Reliance Worldwide Corporation Product Catalog Jun. 2018.

PCT/US2020/061600 filed Nov. 20, 2020 International Search Report and Written Opinion dated Aug. 13, 2021.

PCT/US2021/041467 filed Jul. 13, 2021 International Search Report and Written Opinion dated Oct. 22, 2021.

PCT/US2021/048746 filed Sep. 1, 2021 International Search Report and Written Opinion dated Jun. 1, 2022.

PCT/US2021/049888 filed Sep. 10, 2021 International Preliminary Report on Patentability dated Mar. 5, 2024.

PCT/US2021/049888 filed Sep. 10, 2021 International Search Report and Written Opinion dated Jun. 15, 2022.

PCT/US2023/030967 filed Aug. 23, 2023 International Search Report and Written Opinion dated Mar. 18, 2024.

PCT/US2021/040729 filed Jul. 7, 2021 International Search Report and Written Opinion dated Apr. 7, 2022.

U.S. Appl. No. 18/036,367, filed May 10, 2023 Restriction Requirement dated Jun. 2, 2026.

U.S. Appl. No. 18/690,240, filed Mar. 7, 2024 Non-Final Office Action dated May 19, 2026.

* cited by examiner

FLUID CONNECTOR FOR VASCULAR ACCESS DEVICE

PRIORITY

This application is a U.S. national stage application of International Application No. PCT/US2021/045743, filed Aug. 12, 2021, which claims the benefit of priority to U.S. Provisional Application No. 63/066,003, filed Aug. 14, 2020, each of which is incorporated by reference in its entirety into this application.

BACKGROUND

Current methods of fluidly connecting a vascular access device ("VAD"), e.g. an access port having one or more reservoirs, to a catheter include stretching the catheter over the access port stem. This can be challenging when the catheter, access port and port stem are located within a subcutaneous tissue pocket of a patient. Furthermore, stretching the catheter over the port stem within the subcutaneous pocket can lead to incorrect assembly, slippage, or accidental trauma to the tissue pocket. A more secure connection would allow for higher fluid flow between the catheter and the port while preventing fluid leakage from the connection. Thus, it would be beneficial to couple the catheter and the access port together more quickly, more easily and more securely within the subcutaneous pocket. Disclosed herein is a coupling system and method of use that address the foregoing.

SUMMARY

Disclosed herein is fluid coupling device configured to couple a catheter to an access port including, in some embodiments, a toothed grip connector system configured to retain an end portion of a catheter, the toothed grip connector system further including a recess extending longitudinally from a first end of the coupling device and including an internal stem disposed therein. The fluid coupling device includes a gripping member extending radially about the internal stem and including a plurality of teeth extending radially inward therefrom, the plurality of teeth configured to engage an outer surface of the end portion of the catheter to prevent longitudinal movement in at least a first direction following insertion of the end portion of the catheter into the recess; and a sealing member configured to impinge an outer surface of the catheter to provide a seal between the end portion of the catheter and the internal stem.

In some embodiments, the fluid coupling device further includes a male-end quick connector disposed at a second end thereof, and configured to engage a female-end quick connector coupled to an access port.

In some embodiments, the fluid coupling device includes where the plurality of teeth are angled towards a second end of the coupling device, opposite the first end.

In some embodiments, the fluid coupling device includes where one of the gripping member or the sealing member is retained within a groove in a wall of the recess, the groove extending annularly about the internal stem.

In some embodiments, the fluid coupling device includes a protrusion that extends radially inward from a wall of the recess and is configured to abut against one of the gripping member or the sealing member to inhibit longitudinal movement thereof in at least the first direction.

In some embodiments, the fluid coupling device includes where the sealing member includes one of a silicone, polymer, elastomer, or rubber materials that exhibit watertight properties.

In some embodiments, the fluid coupling device includes where the sealing member is located proximate the first end and the gripping member is located proximate the second end.

In some embodiments, the fluid coupling device includes where the sealing member is located proximate the second end and the gripping member is located proximate the first end.

In some embodiments, the fluid coupling device further includes a tool, a portion thereof configured to extend into the recess between an outer surface of the catheter and a tooth of the plurality of teeth, to disengage the plurality of teeth from the catheter and allow the catheter to be withdrawn along the first longitudinal direction.

Also disclosed is a method for placing a catheter and an access port, including placing the access port into a tissue pocket; positioning a distal end of the catheter at a target location in the patient; inserting a proximal end of the catheter into a toothed grip connector system disposed at a first end of a fluid coupling device, the toothed grip connector system including a recess, an internal stem disposed within the recess, a gripping member extending annularly about the internal stem and a sealing member, the gripping member including a plurality of teeth extending radially inward and configured to engage an outer surface of the catheter to inhibit withdrawal of the catheter from the toothed grip connector system; and providing fluid communication between the catheter and the port.

In some embodiments, the method includes where the fluid coupling device is formed integrally with a port and configured to provide fluid communication thereto.

In some embodiments, the method includes where the second end of the coupling device is configured to engage the port using one of quick connect system, threaded engagement, press-fit, snap fit, adhesive, bonding or welding, to provide fluid communication thereto.

In some embodiments, the method further includes impinging a surface of the sealing member against the outer surface of the catheter; and creating a seal between an inner surface of the catheter and the internal stem.

In some embodiments, the method further includes sliding a disengagement tool into the recess between the plurality of teeth and the outer surface of the catheter; flexing the plurality of teeth radially outward to disengage the outer surface of the catheter; and withdrawing the catheter from the toothed grip connector system.

In some embodiments, the method includes where the gripping member includes a bi-stable configuration including a first stable configuration where the plurality of teeth are angled towards a second end of the fluid coupling device, and a second stable configuration where the plurality of teeth are angled towards a first end of the fluid coupling device.

In some embodiments, the method includes where the second end of the coupling device includes a male-end quick connector configured to couple with a female-end quick connector on the port.

In some embodiments, the method includes where the second end of the coupling device includes a female-end quick connector configured to couple with a male-end quick connector on the port.

Also disclosed herein is a method for connecting a catheter to an access port including creating a port pocket in a patient, placing the access port into the port pocket, the access port including a female connector fitting. The method includes positioning a distal end of the catheter at a target location in the patient, inserting a proximal end of the catheter into a coupling device outside of the port pocket, the coupling device including a first end designed to receive the proximal end of the catheter, the first end including a gripping member to prevent movement of the catheter in the direction away from the coupling device following insertion of the proximal end of the catheter into the first end, and a second end opposite of the first end, the second end including a male connector fitting. The method includes inserting the male connector fitting into the female connector fitting in the port pocket to lock the coupling device to the access port and to place the catheter in fluid communication with the access port.

Also disclosed herein is a fluid coupling system configured to couple a catheter to an access port including a male-end quick connector including an external stem extending along a longitudinal axis and defining a lumen, the stem including a groove extending annularly, and a female-end quick connector defining a lumen and configured to receive the stem of the male-end quick connector. The female-end quick connector includes a collar locking mechanism slidably engaged therewith, the collar locking mechanism transitionable between a locked configuration and an unlocked configuration, and including a tab configured to engage the groove in the locked configuration to releasably retain the stem within the female-end quick connector.

In some embodiments, the fluid coupling system further includes a biasing member configured to bias the collar locking mechanism to the locked position.

In some embodiments, the fluid coupling system further includes a guide structure configured to guide the collar locking mechanism between the unlocked and the locked configuration.

In some embodiments, the fluid coupling system further includes an actuator, disposed of within the lumen of the female-end quick connector and configured to open a valve, the valve configured to control fluid communication between the lumen of the female-end quick connector and the lumen of the male-end quick connector.

In some embodiments, the fluid coupling system includes where the male-end quick connector is coupled to a catheter and the female-end quick connector is coupled to a port.

In some embodiments, the fluid coupling system includes where the female-end quick connector is coupled to a catheter and the male-end quick connector is coupled to a port.

In some embodiments, the fluid coupling system includes where the male-end quick connector is coupled a fluid coupling device including a toothed grip connector system disposed at an opposite end thereof, and configured to engage a catheter.

In some embodiments, the fluid coupling system includes where the collar locking mechanism is slidably engaged with the female-end quick connector along an axis extending parallel to the longitudinal axis.

In some embodiments, the fluid coupling system includes where the collar locking mechanism is slidably engaged with the female-end quick connector along an axis extending perpendicular to the longitudinal axis.

These and other features of the concepts provided herein will become more apparent to those of skill in the art in view of the accompanying drawings and following description, which describe particular embodiments of such concepts in greater detail.

DRAWINGS

DESCRIPTION

Figure 1:
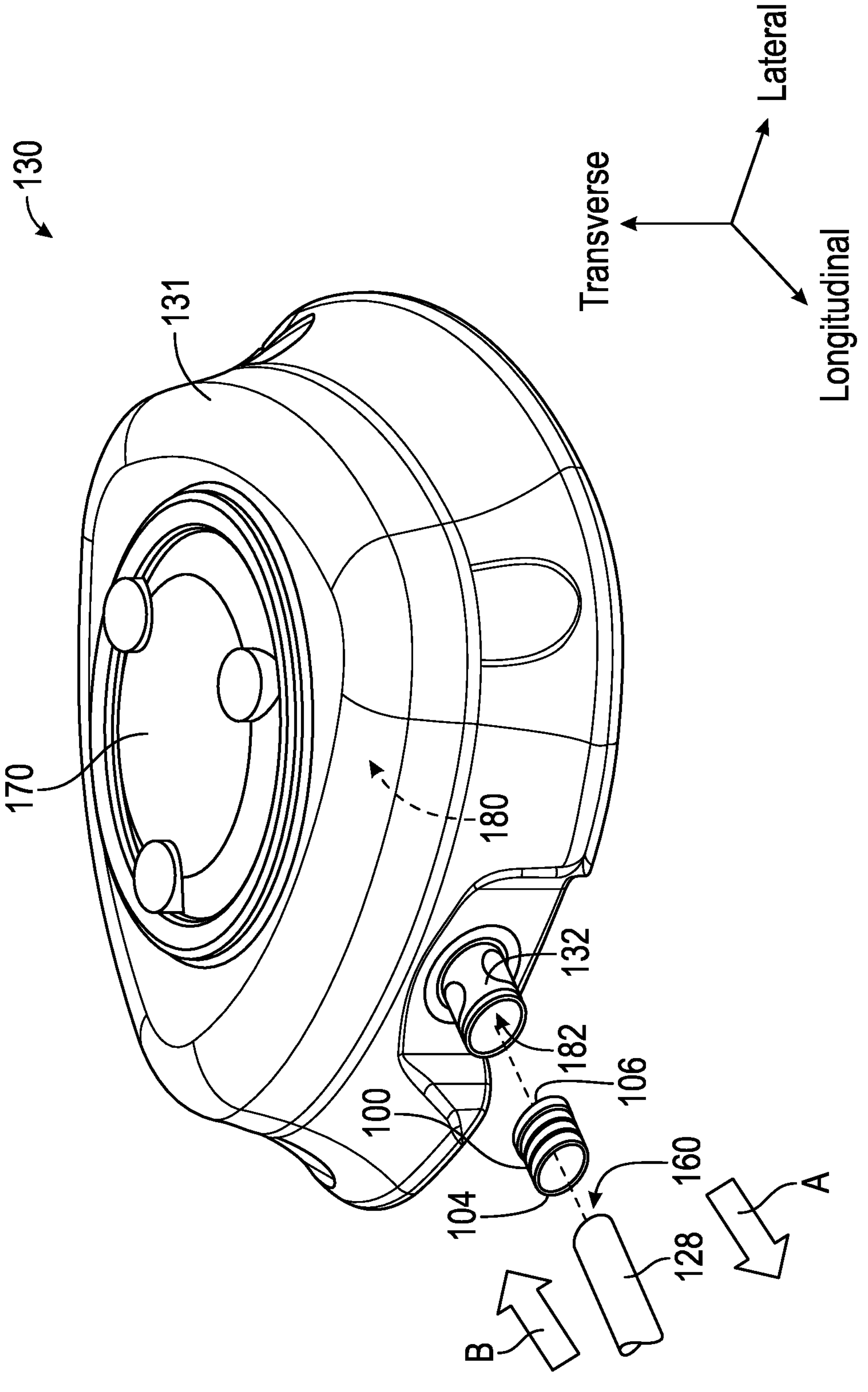
FIG. 1 illustrates an exemplary environment of use including an access port, having a port stem, a coupling system, and a catheter, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

FIG. 1 illustrates a perspective view of an exemplary environment of use for a coupling system ("system") 100 including an access port 130 having an access port stem ("port stem") 132 and a catheter 128 configured to be coupled thereto. In some embodiments, the access port 130 includes a body 131 defining a reservoir 180 and including a needle-penetrable septum 170 disposed thereover. In some embodiments, the port 130 further includes the port stem 132 extending from a side surface of the body 131 and defines a stem lumen 182 that provides fluid communication between a catheter lumen 160 and a reservoir 180. In some embodiments, a catheter 128 can be fluidly coupled to the port 130 by urging the catheter 128 longitudinal over a stem. In an embodiment, the catheter 128 can elastically deform radially outward to stretch over the stem. In an embodiment, a user can replace the catheter 128 by detaching the catheter 128 from the port 130 while the port 130 remains in situ, within a tissue pocket. A new catheter can then be placed and coupled to the port 130. However, stretching the catheter 128 over the port stem in this manner can be challenging, especially when carried out within the tissue pocket.

In an embodiment, a coupling system 100 may be employed to couple the catheter 128 to the port stem 132 in a secure connection to allow for higher fluid flow between the catheter 128 and the port 130 while preventing fluid leakage from the connection. In some embodiments, the coupling system 100 may include a toothed grip connector system 104 configured to couple the catheter 128 to the coupling system 100 and a rapid release connector system 106 configured to couple the port 130 to the coupling system 100. In an embodiment, the coupling system 100 can be coupled to the catheter 128 by urging the coupling system 100 in a first axial direction (A), substantially parallel to a longitudinal axis. The catheter 128 and coupling system 100 can then be connected to the port 130 by urging the catheter 128 and coupling system 100 in a second axial direction (B), substantially parallel to a longitudinal axis.

Figure 2A:
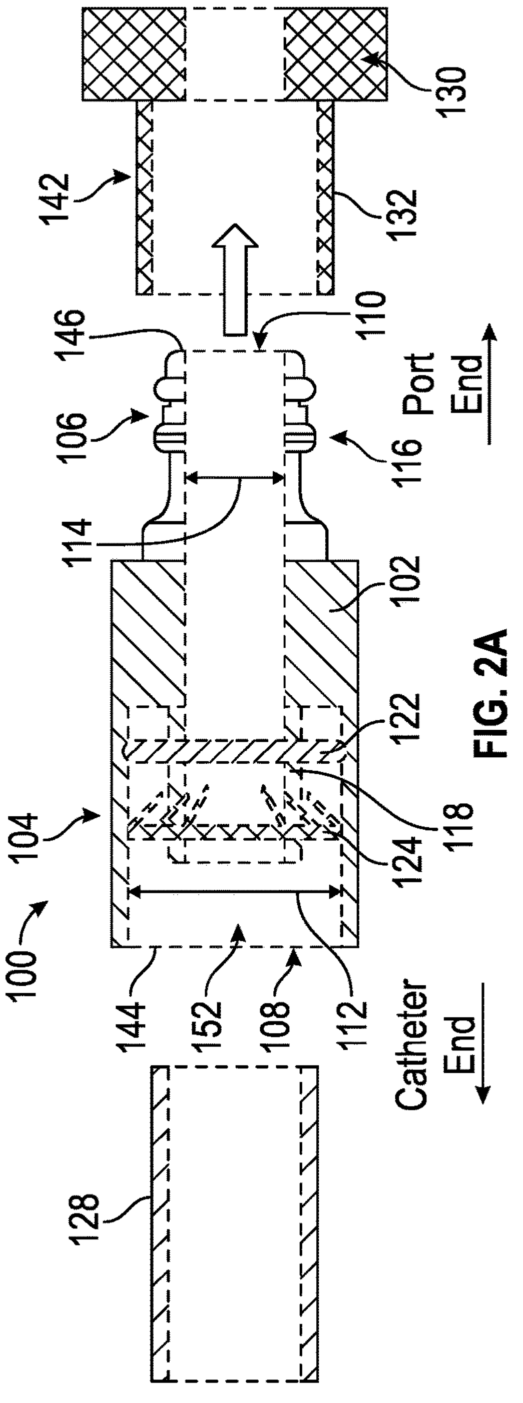
FIG. 2A illustrates a cross-sectional side view of a coupling system, in accordance with some embodiments.
Figure 2B:
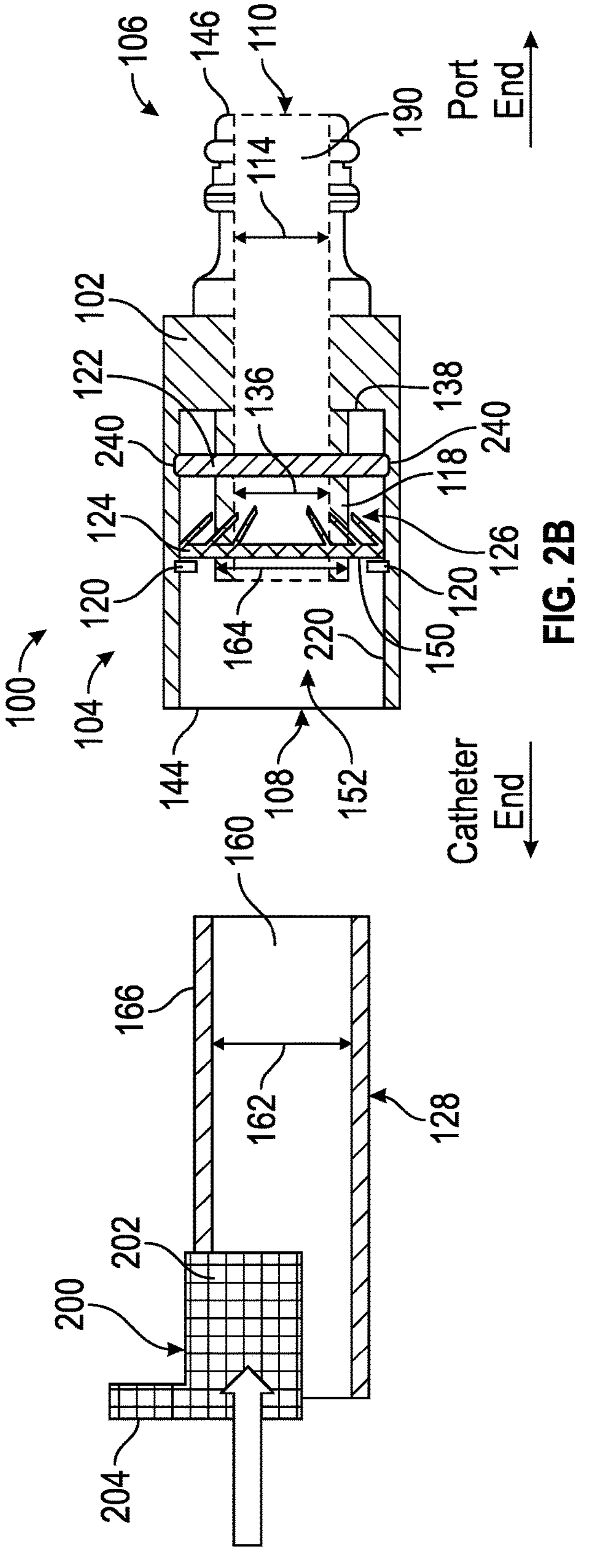
FIG. 2B illustrates a cross-sectional side view of the coupling system, in accordance with some embodiments.

FIGS. 2A-2B show further details of the coupling system 100. FIG. 2A illustrates a cross-sectional side view of the coupling system, ("system") 100 configured to provide fluid communication between the catheter 128 and the port 130. In an embodiment, the coupling system 100 can generally include the toothed grip connector system 104 and the rapid release connector system 106. In an embodiment, the toothed grip connector system 104 can be configured to engage a proximal end of the catheter 128 and the rapid release connector system 106 can be configured to releasably engage the port 130. In an embodiment, the coupling system 100 can be formed integrally with the catheter 128 and can releasably engage the port 130, as described herein. In an embodiment, the coupling system 100 can be formed integrally with the port 130 and can selectively engage the catheter 128, as described herein. In an embodiment, as shown, the toothed grip connector system 104 can be configured to engage the catheter 128 and the rapid release connector system 106 can be configured to engage the port 130. In an embodiment, the toothed grip connector system 104 can be configured to engage the port 130 and the rapid release connector system 106 can be configured to engage the catheter 128. However, it will be appreciated that other numbers or combinations of toothed grip connector systems 104 or rapid release connector systems 106 can be configured to engage one or more of the catheter 128 and the port 130, without departing from the spirit of the invention.

Advantageously, the system 100 can provide a faster, more simplified connection between the catheter 128 and the access port 130 and further mitigates slippage, trauma, and fluid leakage under pressure within the tissue pocket. The connection between the catheter 128, coupling system 100, and stem 132 can be made quickly and with ease within the tissue pocket and ensures proper fluid communication between the catheter 128 and the access port 130.

The system 100 can generally include a connector body ("body") 102 extending between a first end 144 to a second end 146. In some embodiments, the first end 144 is proximate the catheter 128 and the second end 146 is proximate the port stem 132. In an embodiment, the first end 144 can include the toothed grip connector system 104 and the second end 146 can include the rapid release connector system 106. For ease of explanation, embodiments of the coupling system 100 are described in terms of coupling a single lumen catheter. However, it will be appreciated that in some embodiments, the system 100 may be designed to couple two or more lumens of the catheter 128 with two or more lumens of a port stem 132. These and other configurations of multi-lumen catheter connectors are considered to fall within the scope of the present invention.

The toothed grip connector system 104 can generally include a recess 152 having a first opening 108 defining a first opening inner diameter 112. In some embodiments, the first opening inner diameter 112 is bigger than an outer diameter of the catheter 128 and is configured to receive a portion of the catheter 128 therein. In some embodiments, the toothed grip connector system 104 may be configured to selectively secure a portion of the catheter 128 within the recess 152 and provide a fluid tight seal between the catheter 128 and the coupling system 100, as will be described in more detail herein. In an embodiment, the rapid release connector system 106 can generally include a second opening 110 defining a second opening inner diameter 114. In some embodiments, the second end 146 includes a male-end quick connector 116 that engages a female-end quick connector 142 of the port 130 as part of the rapid release connector system 106, as discussed in more detail herein.

FIG. 2B illustrates a cross-sectional side view of the coupling system 100 that includes the toothed grip connector system 104 disposed at the first end 144. The toothed grip connector system 104 can include the recess 152, an internal stem 118, a gripping member 124, and a sealing member 122. The recess 152 extends longitudinally from the first end 144 of the elongated body 102 to an internal shoulder 138. An internal stem 118, a gripping member 124, and a sealing member 122 may be disposed within the recess 152. The internal stem 118 can extend longitudinally from the internal shoulder 138 towards the first end 144, and defines a portion of a connector body lumen 190. The connector body lumen 190 defined by the internal stem 118 can define an inner diameter 136. In some embodiments, the internal stem inner diameter 136 may be equal to or slightly smaller than the second opening diameter 114 to maintain high fluid flow between the second end 146 and the first end 144. In some embodiments, the connector body lumen 190 extends from the internal stem 118 to the second opening 110. In an embodiment, an outer diameter 164 of the internal stem 118 may be equal to or slightly larger than an inner diameter 162 of the catheter lumen 160. As such, the catheter 128 can fit tightly over the internal stem 118 in an interference fit. Optionally, the internal stem 118 can include a chamfered edge to facilitate engagement with the catheter lumen 162.

In some embodiments, the gripping member 124 includes a gripping member ring ("ring") 150 and a plurality of teeth ("teeth") 126 that extends radially inward therefrom and are angled with respect to the longitudinal axis. In an embodiment, the teeth 126 are angled towards the first end 144, towards the second end 146, or combinations thereof. In an embodiment, the gripping member 124 can be configured to allow the teeth 126 to flex radially outward from a resting position. As the catheter 128 is urged into the first end 144, the teeth 126 can flex radially outward to receive the catheter 128 therebetween.

In some embodiments, one or both of the teeth 126 and the gripping member ring 150 can be constructed of the same material. In some embodiments, one or both of the gripping member ring 150 and the teeth 126 can be formed of a plastic, a polymer, a metal, an alloy, a composite, combinations thereof, or the like, and can provide resilient or rigid mechanical properties. In an embodiment, the teeth 126 can be formed of a first material and the gripping member ring 150 can be formed of a second material. For example, in some embodiments, the gripping member 124 can be stamped from a single piece of metallic material, or can be stamped from multiple pieces of metallic material and attached together by adhesive, bonding, welding, or the like. In some embodiments, the gripping member 124 can be injection molded or 3D printed from a plastic, synthetic polymer, or the like. In some embodiments, the gripping member ring 150 may be constructed of a flexible material, while the plurality of teeth 126 may be constructed of a rigid metallic material and coupled to the gripping member ring 150. In some embodiments, the flexibility of the gripping member ring 150 can allow for the teeth 126 to be to be flexed radially outward to allow for removal of the catheter 128 from the coupling system 100.

In an embodiment, the teeth 126 may be angled towards the second end 146. This allows the catheter 128 to be urged inwards into the recess 152 and received between the teeth 126. The teeth 126 may then engage an outer surface 166 of the catheter 128 and retain a portion of the catheter 128 between the teeth 126 and the internal stem 118 to inhibit withdrawal of the catheter 128 from the recess 152. In some embodiments, the teeth 126 may or may not contact the internal stem 118.

In an embodiment, the user can insert a disengagement tool 200 into the first end 144 to release the catheter 128 from toothed grip connector system 104. For example, as shown in FIGS. 2B and 5D, the disengagement tool 200 can extend annularly about a portion of the outer surface 166 of the catheter 128 and slide into the toothed grip connector system 104 between the plurality of teeth 126 and the outer surface 166 of the catheter 128. In some embodiments, the disengagement tool 200 includes a sliding portion 202 and a handle portion 204 connected to the sliding portion 202. In some embodiments, the sliding portion 202 is configured to slide along the outer surface 166 of the catheter 128 and fit between the outer surface 166 of the catheter 128 and the plurality of teeth 126 when the catheter 128 is disposed within the first end 144. The sliding portion 202 can be urged into the toothed grip connector system 104 to flex the teeth 126 radially outward and allow the catheter 128 to be released therefrom.

In an embodiment, the disengagement tool 200 can be a separate structure from the toothed grip connector system 104 and engaged therewith to disengage the catheter 128, as described herein. In an embodiment, the disengagement tool 200 can be slidably coupled with the toothed grip connector system 104 and can be actuated by a button or similar mechanism to disengage the catheter 128.

In an embodiment, the gripping member 124 can include a bi-stable configuration where in a first stable configuration the plurality of teeth 126 are angled towards the second end 146 (e.g. as shown in FIG. 2B) and in a second stable configuration, the plurality of teeth 126 are angled towards the first end 144. In an embodiment, in the first stable configuration, with the catheter 128 retained therebetween, the gripping member 124 can inhibit movement of the catheter 128 towards the first end 144 when a first axial force is applied thereto. However, when a second axial force is applied, which is greater than the first axial force, the gripping member 124 can transition from the first stable configuration to the second stable configuration to allow the catheter 128 to be withdrawn from the recess 152. Similarly, the gripping member 124 in the second stable configuration can receive an end portion of the catheter 128. A user can apply the second axial force to urge the catheter 128 into the recess 152 and transition the gripping member 124 from the second stable configuration to the first stable configuration to retainer the catheter 128, as described herein.

In some embodiments, the toothed grip connector system 104 includes a sealing member 122. The sealing member 122 defines a substantially toroidal shape and can be made of silicone, polymer, elastomer, rubber, synthetic polymers, plastics, organic non-plastic polymers, rubber alternatives or other materials that are able to form a fluid tight seal between the catheter 128 and an inner wall 220 of the recess 152. In some embodiments, the gripping member 124 and sealing member 122 are disposed annularly about the internal stem 118 within the recess 152. In some embodiments, an outer perimeter of one of the gripping member 124, the sealing member 122, or both are retained within an annular groove 240 disposed in the inner wall 220 of the recess 152. In an embodiment, one or both of the gripping member 124 and the sealing member 122 can be retained within the recess 152 or within the annular groove 240 with adhesive, welding, bonding, interference fit, press-fit, or snap-fit engagement. In some embodiments, in a disengaged state, the teeth 126 can engage the internal stem 118 to retain the gripping member 124 within the recess. In an embodiment, in a disengaged state as illustrated in FIG. 2B, the teeth 126 can be in a spaced apart relationship relative to the internal stem 118.

In some embodiments, the gripping member 124 can be coupled to the sealing member 122 by adhesive, bonding, welding, or the like. In some embodiments, the gripping member 124 can also be configured to provide a fluid tight seal between the catheter 128 and the internal stem 118. For example, the gripping member ring 150 can include a silicone rubber material, or the like, and can include a plurality of teeth 126 extending radially therefrom, as described herein. In an embodiment, the gripping member ring 150 provides the sealing action and the plurality of teeth 126 provide the gripping action. In an embodiment, the gripping member 124 or the sealing member 122 can be secured in place by at least one protrusion 120, or similar mechanical means. In some embodiments, the protrusion 120 extends radially inward from the inner wall 220 of the recess 152 and is configured to abut against the gripping member 124 to inhibit longitudinal movement thereof. In some embodiments, the at least one protrusion 120 is configured to abut against the sealing member 122 to inhibit longitudinal movement thereof. In an embodiment, one of the gripping member 124 or the sealing member 122 can be secured in place by an adhesive, welding, bonding, combination thereof, or the like.

Figure 2C:
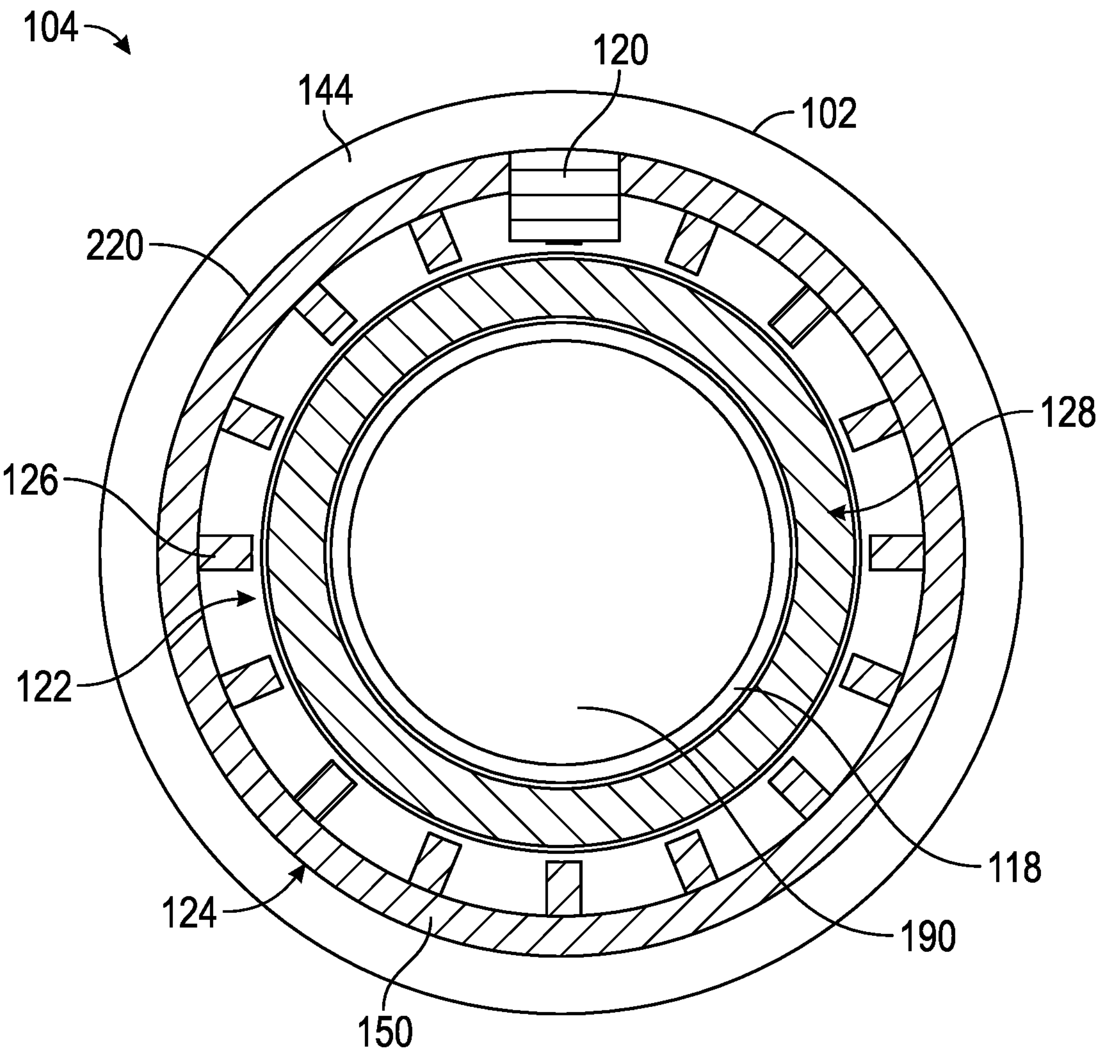
FIG. 2C illustrates a catheter end view of a toothed grip connector system, in accordance with some embodiments.

FIG. 2C illustrates a catheter end view of the toothed grip connector system 104, in accordance with some embodiments. The toothed grip connector system 104 includes the recess 152 and the inner wall 220 thereof. The recess 152 further includes the sealing member 122, the gripping member 124 disposed between the first end 144 and the sealing member 122. The toothed grip connector system 104 further includes the internal stem 118, and the at least one protrusion 120 configured to abut against the gripping member 124 to inhibit longitudinal movement thereof. In some embodiments, the gripping member 124 is disposed proximate the first end 144 and the sealing member 122 is disposed proximate the second end 146. In some embodiments, the gripping member 124 can be disposed proximate the second end 146 and the sealing member 122 can be disposed proximate the first end 144.

Figure 3A:
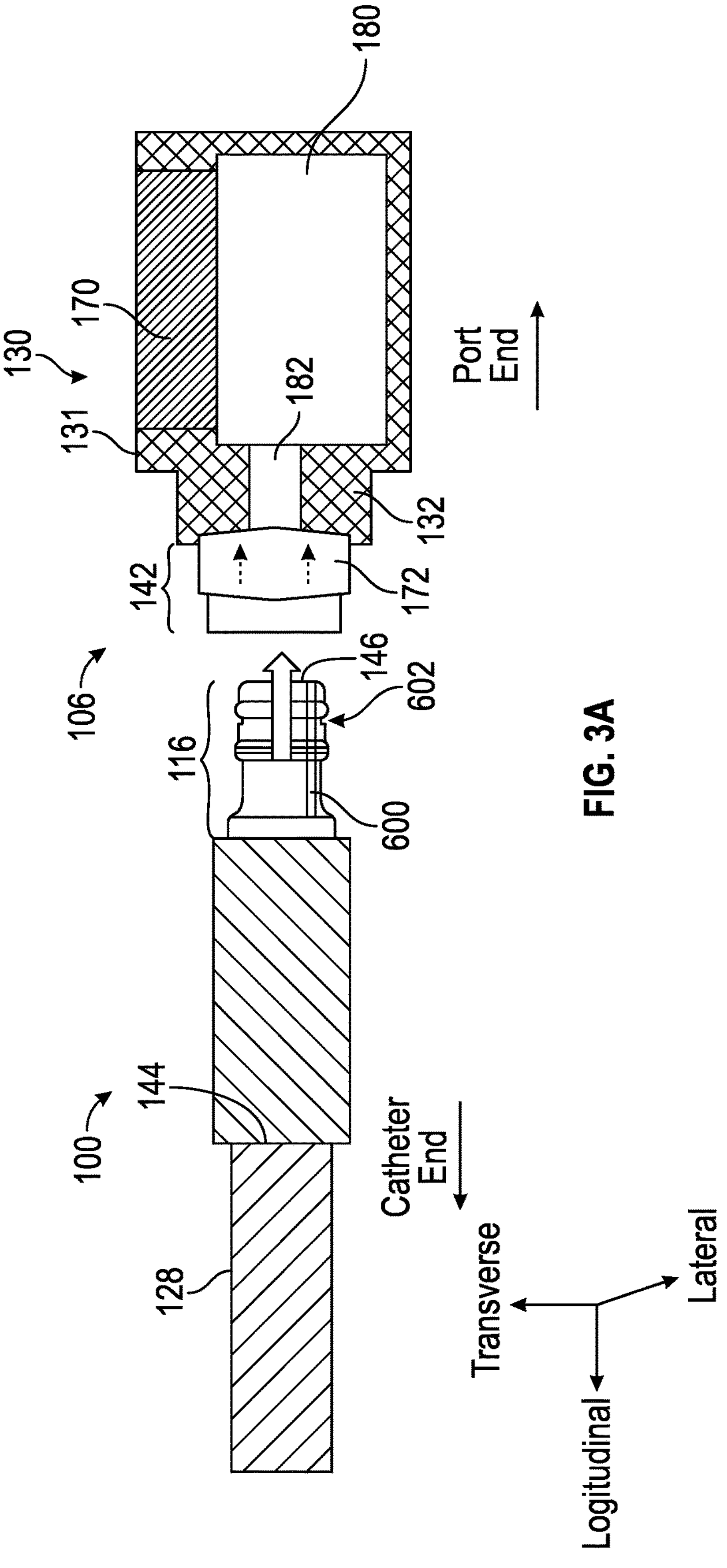
FIGS. 3A-3B illustrates a side view of a fluid coupling device coupled to a catheter and engaging an access port, in accordance with some embodiments
Figure 3B:
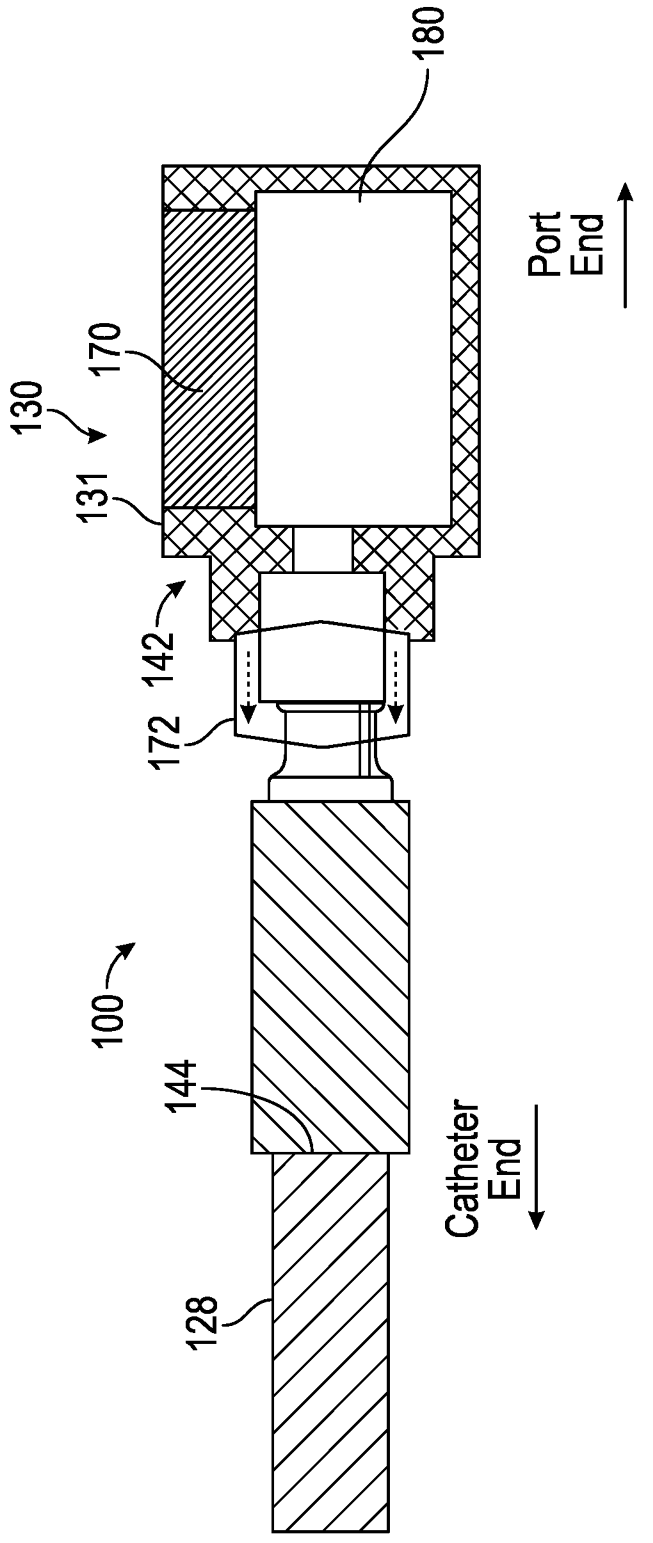

FIGS. 3A-3B illustrates a side view of the coupling system 100 engaged with a catheter 128, and including the rapid release connector system 106 configured to couple the coupling system 100 with the access port 130, or similar VAD. In some embodiments, the access port 130 can be disposed within a subcutaneous tissue pocket 134 and the coupling system 100/catheter 128 assembly can be coupled thereto within the tissue pocket 134. In some embodiments, the coupling system 100 can be attached to the port 130 within the tissue pocket 134. The catheter 128 can then be coupled to the coupling system 100 within the tissue pocket 134. In some embodiments, the coupling system 100 can be releasably coupled to the access port stem 132. In some embodiments, the coupling system 100 can be formed integrally with the port 130, such that the coupling system 100 is in place of the port stem 132 and provides fluid communication between the catheter 128 and the reservoir 180 of the access port 130, for example by way of an access port lumen 182.

In some embodiments, the rapid release connector system 106 can couple the coupling system 100 to the access port 130. For example, the rapid release connector system 106 includes a male-end quick connector 116, disposed on the coupling system 100, and is configured to slidably engage the female-end quick connector 142, disposed on the access port 130, to provide fluid communication between the catheter 128 and the access port 130. In some embodiments, the male-end quick connector 116 can include an external stem extending longitudinally and including a chamfered edge to facilitate engagement. In some embodiments, the male-end quick connector 116 including the external stem includes a groove 600, extending longitudinally and configured to facilitate alignment of the male-end quick connector 116 within the female-end quick connector 142. The female-end quick connector 142 include a recess extending longitudinally and configured to receive the male-end quick connector 116 therein.

In some embodiments, the female-end quick connector 142 can be disposed on the coupling system 100 and the male-end quick connector 116 can be disposed on the access port 130. In an embodiment, the system 100 can be coupled to the port 130 with a threadable engagement, interference fit, press-fit, or snap-fit engagements, combinations thereof, or the like. In an embodiment, the coupling system 100 can be integrally formed with the port 130. In an embodiment, the coupling system 100 can be attached to the port 130 using adhesive, bonding, welding, or the like.

As illustrated in FIGS. 3A-3B, in some embodiments, the female-end quick connector 142 includes a collar locking mechanism 172 slidably engaged therewith along a longitudinal axis and can transition the female-end quick connector 142 between a locked configuration (FIG. 3B) and an unlocked configuration (FIG. 3A). In an unlocked configuration, the male-end quick connector 116 of the catheter coupling system 100 can be inserted into, and withdrawn from, the female-end quick connector 142 along a longitudinal axis. The collar locking mechanism 172 can transition from the unlocked configuration to the locked configuration, to retain the male-end quick connector 116 within the female-end quick connector 142, coupling the port 130 with the catheter 128 and the coupling system 100 and providing fluid communication therebetween. Exemplary locking mechanisms between the female-end quick connector 142 and the male-end quick connector 116 can include pinions and grooves, locking lugs, bayonet locking mechanism, collet chuck locking mechanism, or the like.

Figure 4A:
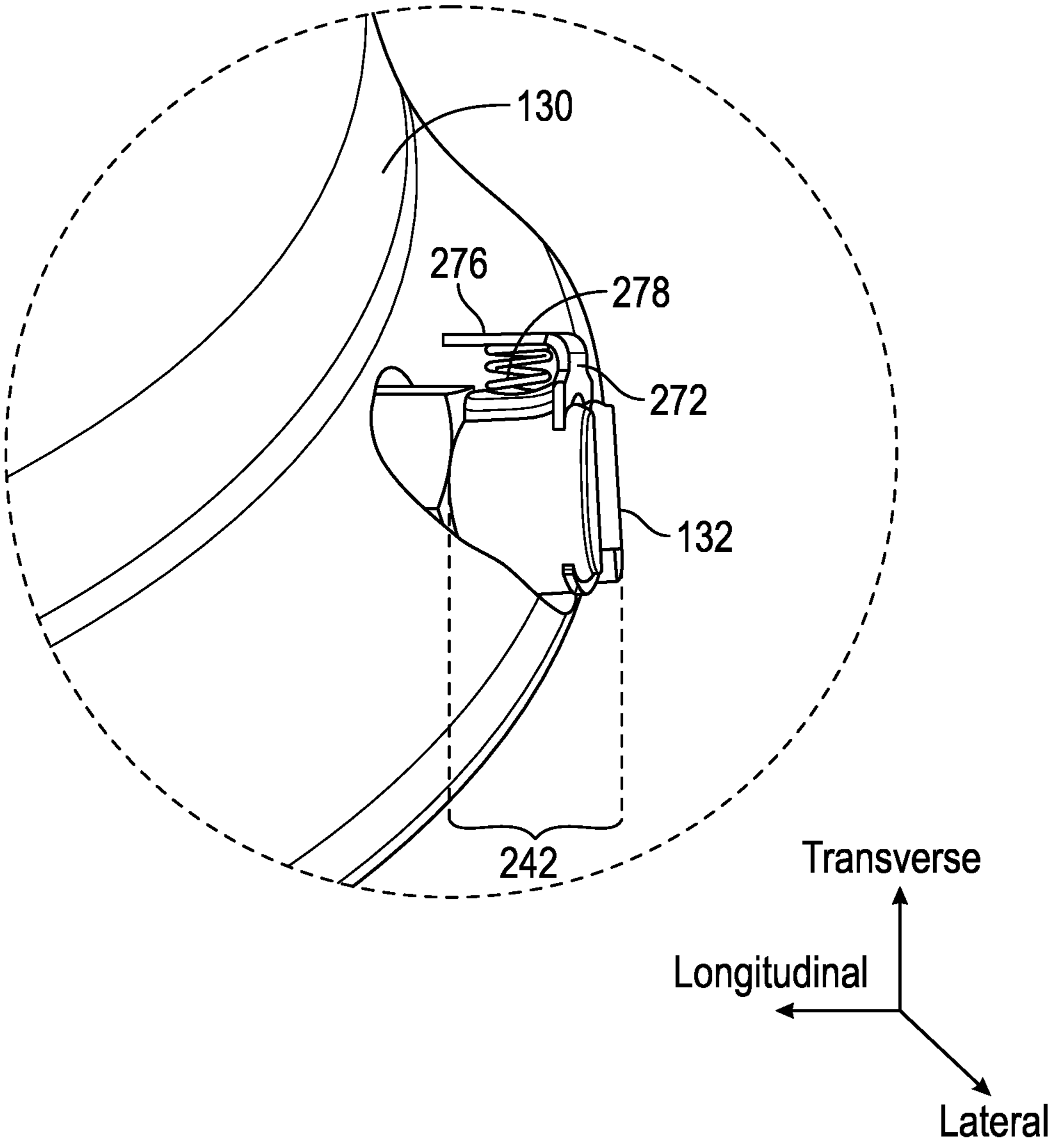
FIG. 4A illustrates a side view of an access port including female-end quick connector of the rapid release connector system, in accordance with some embodiments.
Figure 4B:
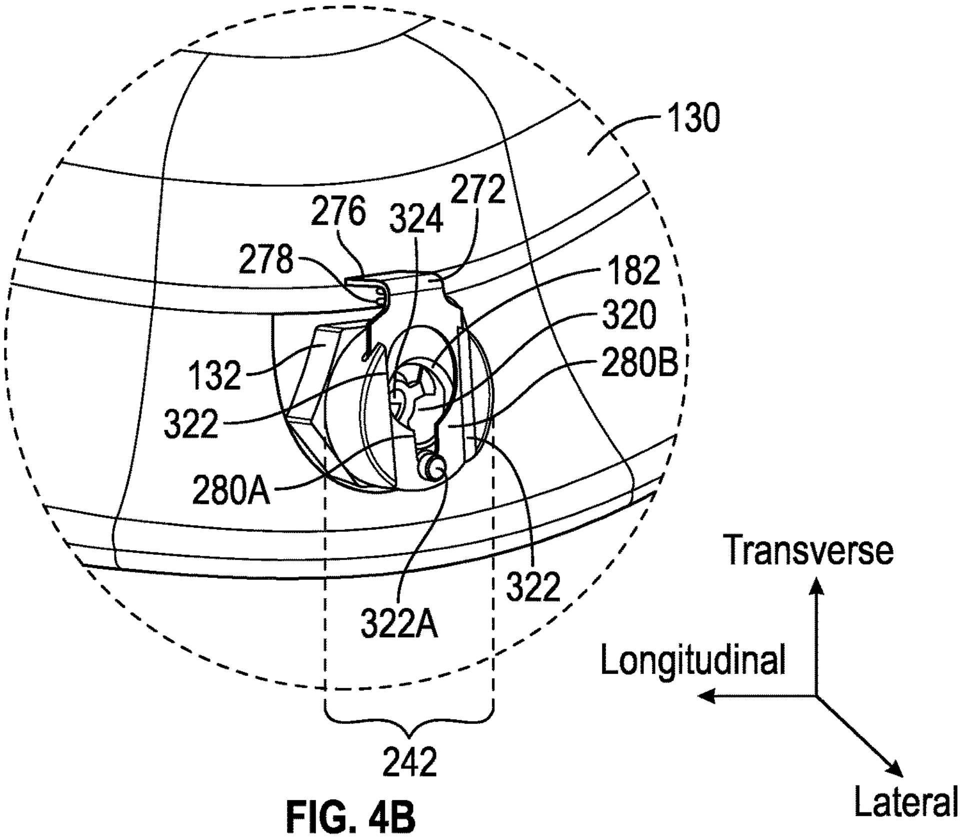
FIG. 4B illustrates perspective view of the access port of FIG. 4A including the female-end quick connector in a locked configuration, in accordance with some embodiments.
Figure 4C:
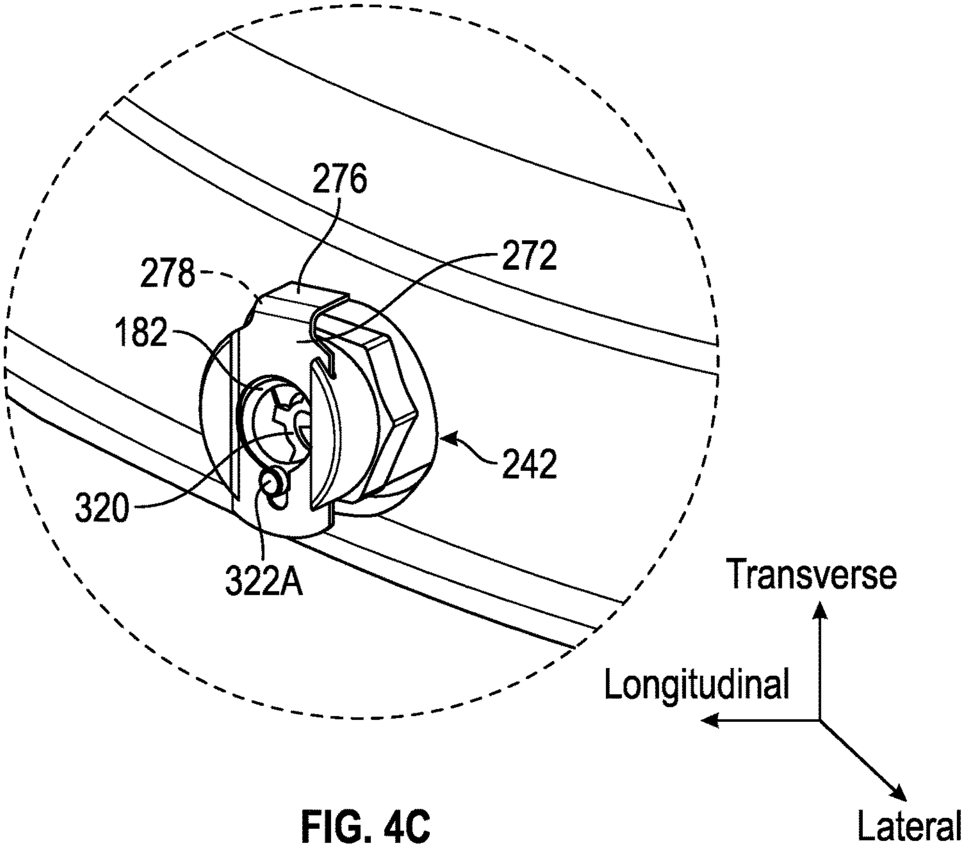
FIG. 4C illustrates an end view of the access port of FIG. 4A including the female-end quick connector in an unlocked configuration, in accordance with some embodiments.

FIGS. 4A-4C show various views of an embodiment of a female-end quick connector 242. FIG. 4A illustrates a side view of the female-end quick connector 242 of the rapid release connector system 106, coupled to the access port 130. FIG. 4B shows a perspective view of the female-end quick connector 242 in a locked, or closed position. FIG. 4C shows a perspective view of the female-end quick connector 242 in an unlocked, or open position. The female-end quick connector 242 can be coupled to the access port 130, as described herein. In an embodiment, the female-end quick connector 242 includes a collar locking mechanism 272 further including a collar locking tab 276 and a collar locking spring 278. The collar locking mechanism 272 can be slidably engaged with the female-end quick connector 242 along an axis extending perpendicular to the longitudinal axis. For example, the locking tab 276 can slide along a transvers axis between a locked and an unlocked position. A biasing member 278, e.g. a spring or the like, can bias the collar locking mechanism 272 to the locked position.

FIG. 4B illustrates a perspective view of the access port 130 of FIG. 4A including the female-end quick connector 242 in a locked configuration, in accordance with some embodiments. The collar locking mechanism 272 can include one or more tabs 280 e.g. first tab 280A and second tab 280B. The tabs 280A and 280B can slidably engage a groove 602 or abutment extending annularly about the male-end quick connector 116 to retain the male-end quick connector 116 within the female-end quick connector 242.

In an embodiment, the access port lumen 182 includes a port valve 324 coupled with an actuator 320. When the male-end quick connector 116 engages the female-end quick connector 242, a tip of the male-end quick connector 116, e.g. second end 146, contacts the actuator 320 and opens the port valve 324. In an embodiment, the actuator 320 can align the connector body lumen 190 of the coupling system 100 with the lumen of the female-end quick connector 242

In an embodiment, the female-end quick connector 242 can include one or more guide structures 322 configured to guide the collar locking mechanism 272 transversely between an unlocked configuration and a locked configuration. In this embodiment, the guide structure 322 can include a rounded cylindrical protrusion 322A that extends longitudinally from the female-end quick connector 242 and slidably engages the collar locking mechanism 272. In an embodiment the protrusion 322A can be coupled to one of the actuator 320 or the port valve 324. A portion of the male-end quick connector 116 can depress the cylindrical protrusion 322A when engaged with the female-end quick connector 242 and open the port valve 324. As shown, the collar locking spring 278 biases the collar locking tab 276, and thus the collar locking mechanism 272, towards the locked configuration.

FIG. 4C illustrates the female-end quick connector 242 of FIG. 4A in an unlocked configuration. In this embodiment, the collar locking spring 278 is transversely compressed by the collar locking tab 276, allowing the collar locking mechanism to slide along the guide structure(s) 322 to the unlocked configuration and to allow engagement with the male-end quick connector 116.

Figure 5A:
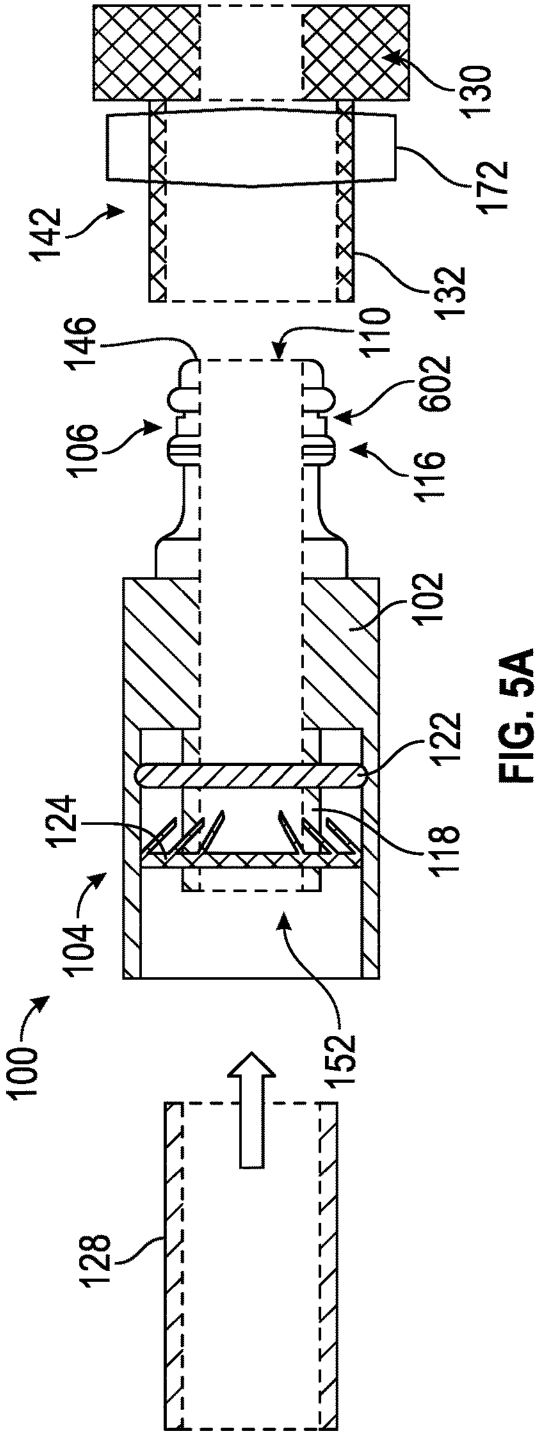
FIGS. 5A-5D illustrate a cross-sectional side view of an exemplary method of coupling a catheter to an access port using the coupling system, in accordance with some embodiments.
Figure 5B:
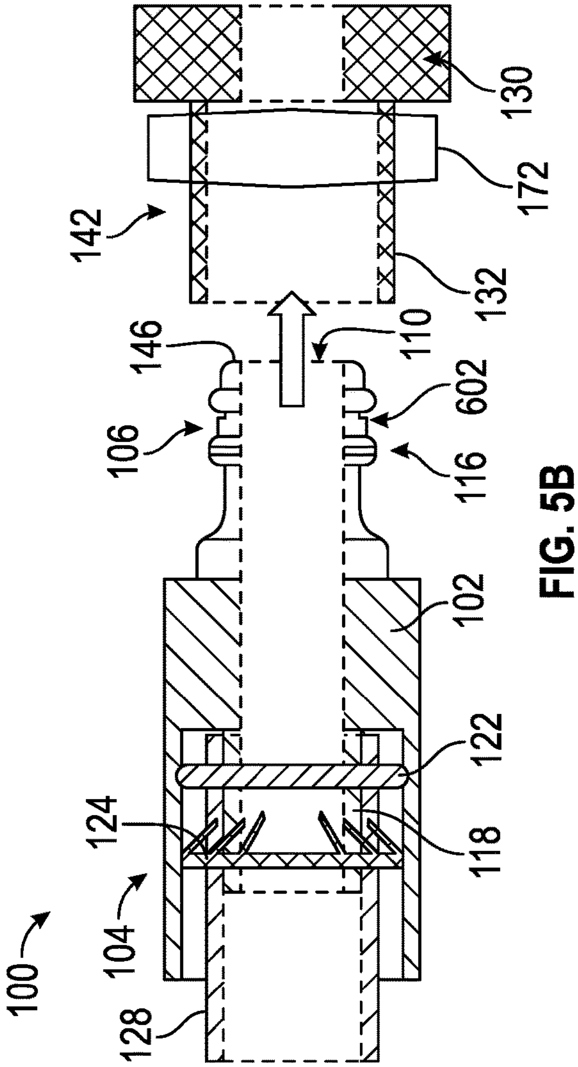
Figure 5C:
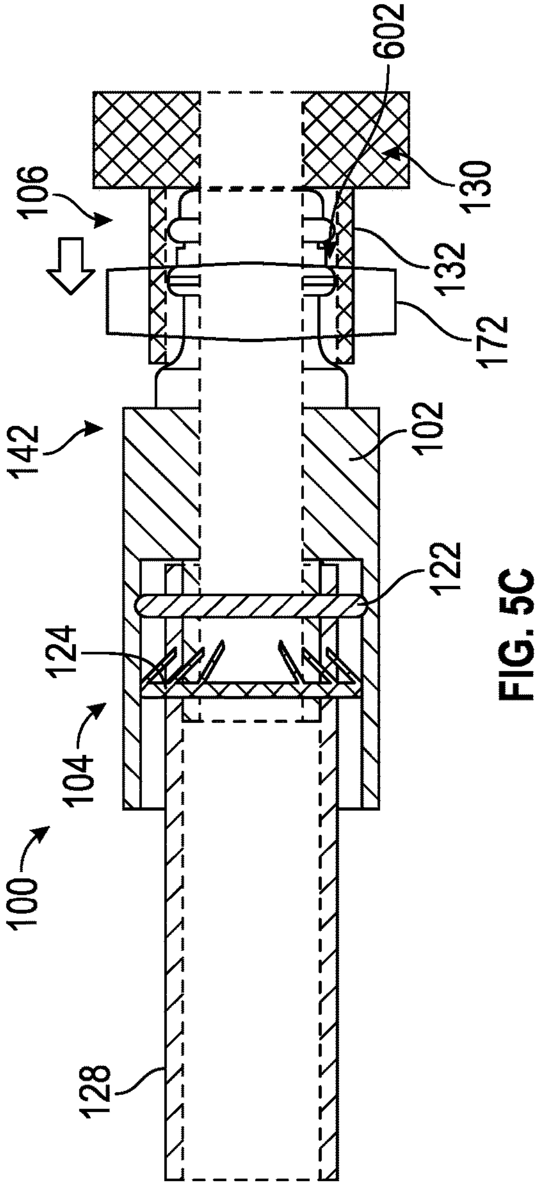
Figure 5D:
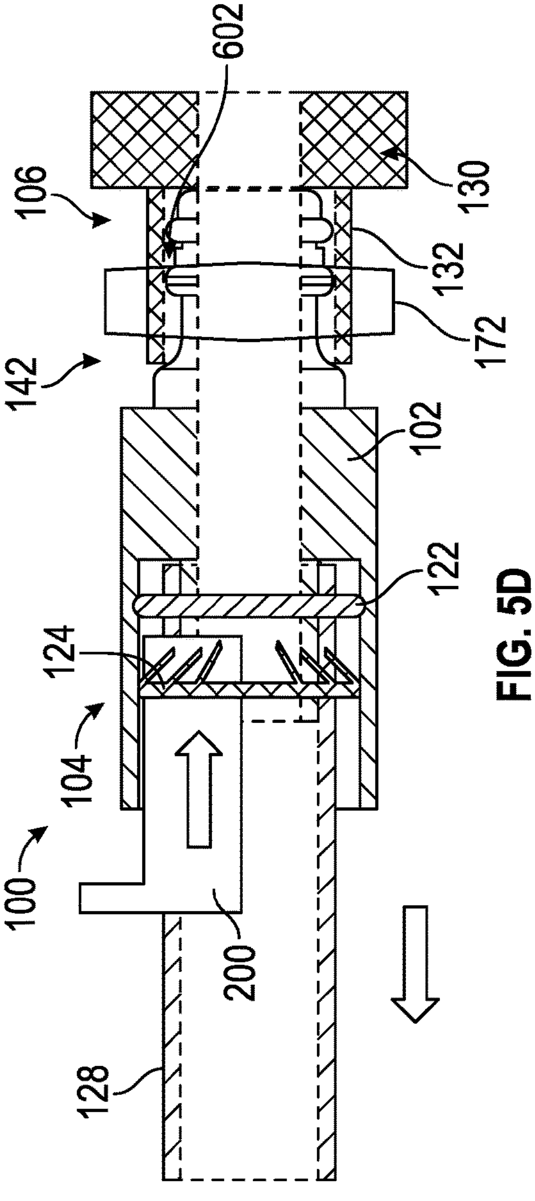

FIGS. 5A-5D illustrates a cross-sectional side view of an exemplary method for coupling a catheter 128 to an access port 130 using the coupling system 100, in accordance with some embodiments. In an embodiment, the catheter 128 can be coupled to a fluid device outside a tissue pocket 134 of a patient. In FIG. 5A, the catheter 128 can be inserted into toothed grip connector system 104 of the coupling system 100, and coupled thereto as described herein. As illustrated in FIG. 5B, the catheter 128 is advanced into the recess 152. The catheter lumen 160 receives the internal stem 118 therein such that the catheter 128 is disposed over the internal stem 118. The proximal end of the catheter 128 extends through the gripping member 124 and the sealing member 122 and can engage the internal shoulder 138. The plurality of teeth 126 of the gripping member 124 engages the outer surface 166 of the catheter 128. In an embodiment, the plurality of teeth 126 can be angled towards the second end 146 so as to grip into the outer surface 166 of the catheter 128 and inhibit withdrawal of the catheter 128 from the recess 152.

In an embodiment, the sealing member 122 can engage the outer surface 166 of the catheter 128 and provides a seal between the catheter 128 and the body 102 of the coupling system 100. In an embodiment, the sealing member 122 can compress the portion of the catheter 128 radially inward onto the internal stem 118 and create a seal therebetween. As shown in FIG. 5B, the gripping member 124 opposes any forces applied to the catheter 128 to mitigate the disengagement of the catheter 128 from the coupling system 100. The plurality of teeth 126 of the gripping member 124 engage the catheter 128 and the protrusion 120 prevents longitudinal movement of the gripping member 124 which together prevents the catheter 128 and gripping member 124 from being withdrawn longitudinally and disengaging the internal stem 118. In an embodiment, the gripping member 124 or the sealing member 122 can be disposed within the annular groove 240 disposed in the inner wall 220 of the recess 152.

As shown in FIGS. 5B-5C, the catheter 128 and coupling system 100 can then be urged longitudinally to engage the male-end quick connector 116 with a female-end quick connector 142, 242, e.g. collar locking female-end quick connector 142. The collar locking mechanism 172 can then transition to the locked position to secure the male-end quick connector 116 within the female-end quick connector 142. In an embodiment, the collar locking mechanism 172 can be transitioned from the locked position to the unlocked position to selectively release the male-end quick connector 116 from the female-end quick connector 142.

In an embodiment, as shown in FIG. 5D, a disengagement tool 200 can be slid between the outer surface 166 of the catheter 128 and the teeth 126. The disengagement tool 200 can be configured to flex the teeth 126 radially outward to disengage the outer surface 166 of the catheter 128 and allow the catheter 128 to be withdrawn from the recess 152 of the coupling system 100. To note, the gripping member 124 can be configured such that flexing one or more teeth of the plurality of teeth 126 can cause all of the plurality of teeth 126 to flex concurrently. In an embodiment, the toothed grip connector system 104 further includes a mechanism (not shown) that, when actuated, flexes the plurality of teeth 126 radially outward to disengage the outer surface 166 of the catheter 128 and allow the catheter 128 to be withdrawn from the recess 152.

Figure 6:
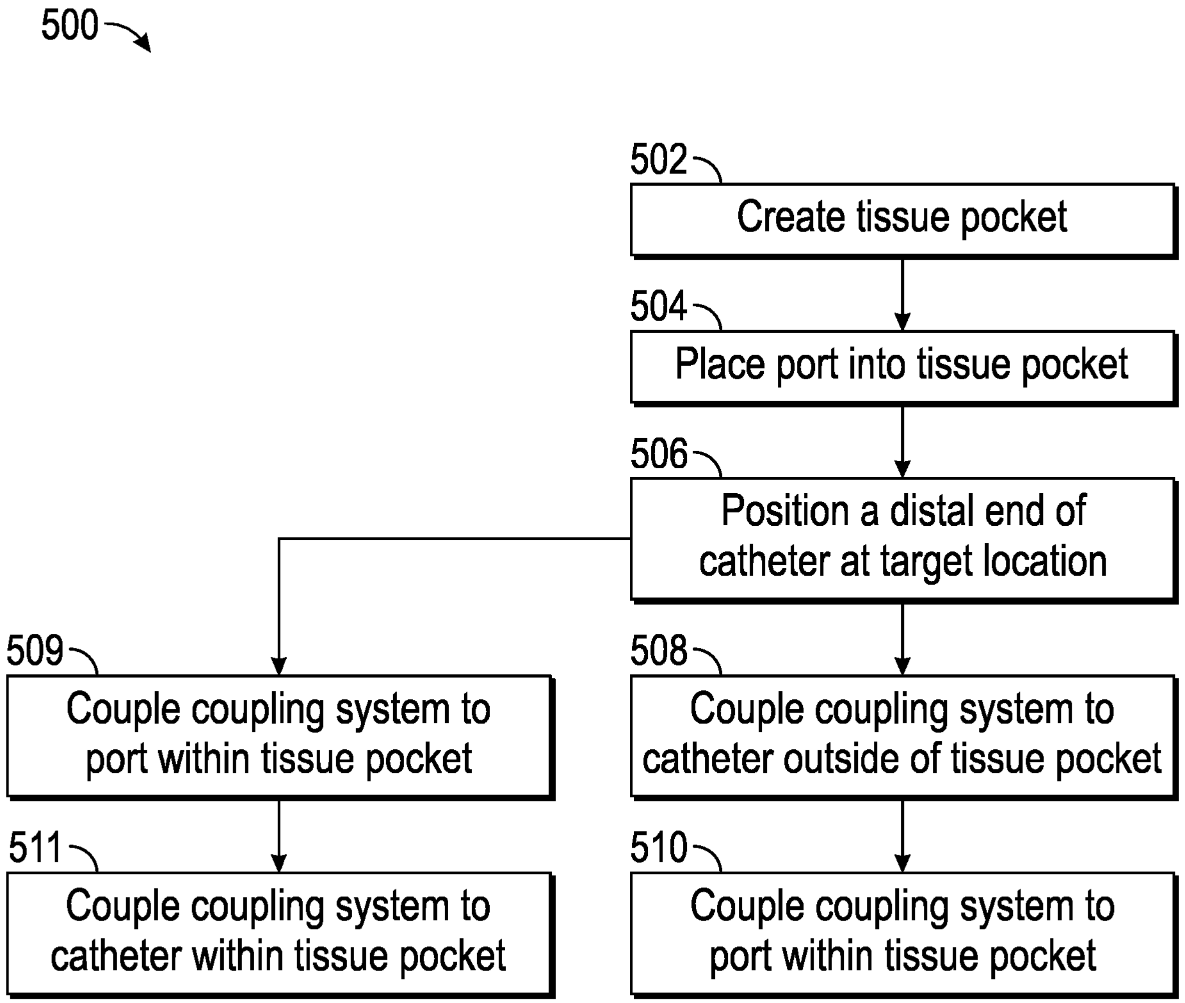
FIG. 6 illustrates a flow chart of an exemplary method of use of the coupling system, in accordance with some embodiments.
Figure 7A:
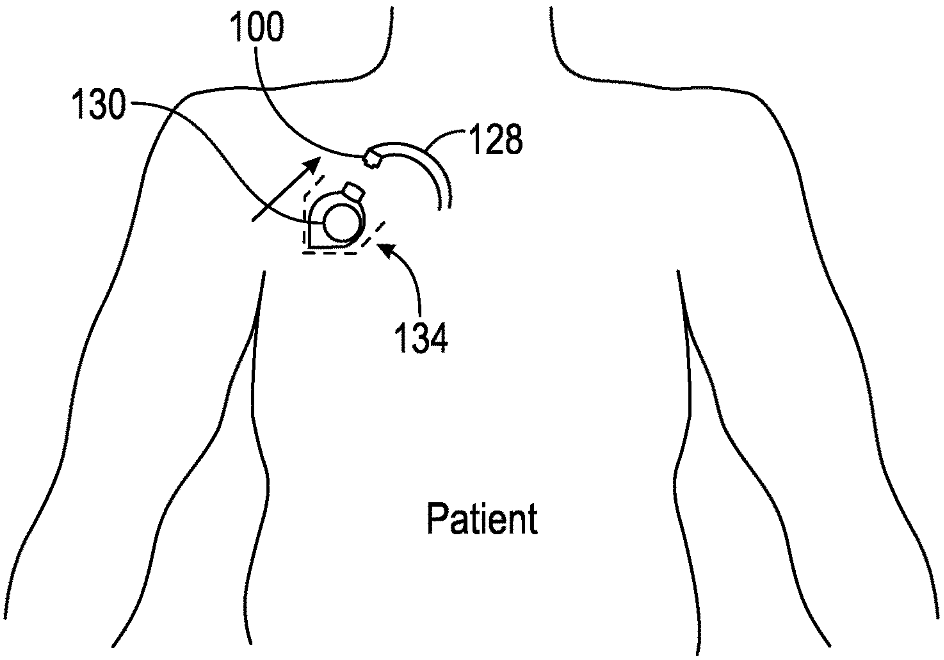
FIGS. 7A-7B illustrates an exemplary environment of use including the coupling system coupling a catheter to an access port within a tissue pocket, in accordance with some embodiments.
Figure 7B:
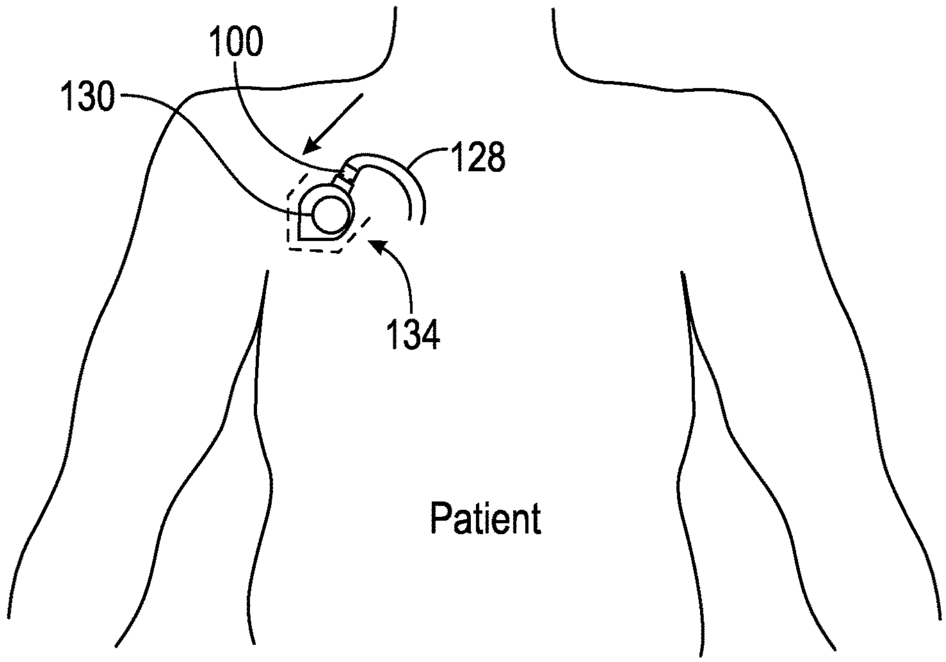

FIGS. 6-7B show an exemplary method of use for the coupling system 100. Referring to FIG. 6, a flowchart illustrates an exemplary method for use of a coupling system 100, in accordance with some embodiments. Each block illustrated in FIG. 6 represents an operation performed in the method 500 of use of a coupling system 100. As an initial step in the method 500, a tissue pocket 134 is created in a patient (block 502). In some embodiments, the tissue pocket 134 can be created in the chest wall of the patient and can be configured to the size of the respective port 130. However, it will be appreciated that this is exemplary and that the tissue pocket 134 can be created anywhere on the patient.

In the next step in the method 500, the access port 130 is placed and secured into the tissue pocket 134 (block 504). In some embodiments, the access port 130 includes a female-end quick connector 142 that is configured to attach to a male-end quick connector 116. In some embodiments, the access port 130 includes a male-end quick connector 116 that is configured to attach to the female-end quick connector 142.

The next step in the method 500 includes positioning a distal end of the catheter 128 at a target location within the vasculature of the patient (block 506). For example, in some embodiments, the distal end of the catheter 128 may be positioned within the Inferior Vena Cava (IVC), or the like.

In an embodiment, the method 500 includes inserting a proximal end of the catheter 128 into a toothed grip connector system 104 of the coupling system 100 outside of the tissue pocket 134 (block 508). Optionally, a proximal portion of the catheter 128 may be trimmed to an appropriate length to facilitate engagement with the coupling system 100/port 130. Advantageously, the catheter 128 can be sized to the exact length while positioned within the patient. This contrasts with estimating an appropriate length of the catheter prior to placement which can lead to misalignment of the catheter within the vasculature.

The toothed grip connector system 104 includes a gripping member 124 configured to prevent withdrawal of the catheter 128 from the toothed grip connector system 104 as described herein, and a sealing member 122 configured to create a fluid tight seal between the catheter 128 and the internal stem 118. Advantageously, the proximal end of the catheter 128 can be urged into the coupling system 100 with less force than is required to stretch the catheter 128 over a port stem 132. This allows for correct assembly of the catheter 128/port 130 while ensuring a secure, fluid tight seal and a reduced chance of slippage and trauma fluid leakage under pressure to the tissue pocket during placement.

In an embodiment, a final step in the method 500 includes inserting the second end 146 of the coupling system 100 including the rapid release connector system 106 further including a male-end connector 116 into the female-end connector 142 of the port stem 132 within the tissue pocket 134 and securing a collar 172, 272 to lock the coupling system 100 to the port 130 to place the catheter 128 in fluid communication with the access port 130 (block 510).

In some embodiments, the method 500 includes a step of inserting the second end 146 that includes the rapid release connector system 106, into the port 130 within the tissue pocket 134 (block 509).

In some embodiments, the method 500 includes a last step of inserting the catheter 128 into the toothed grip connector system 104 of the coupling system 100 within the tissue pocket 134 to place the catheter 128 in fluid communication with the access port 134 (block 511).

FIGS. 7A-7B further illustrates an exemplary environment of use for the port 130 disposed within a tissue pocket 134 of a patient and the catheter 128 coupled to the coupling system 100. In some embodiments as illustrated in FIG. 7A, the port 130 and the catheter 128 have both been implanted in the patient but the port 130 is not yet coupled to the coupling system 100 although both are disposed within the tissue pocket 134. As shown in FIG. 7B the port 130 can then be coupled to the coupling system 100 within the tissue pocket 134 of the patient, providing fluid communication between the catheter 128 and the port 130.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A coupling system configured to couple a catheter to an access port, the coupling system comprising:
- a toothed grip connector system configured to retain an end portion of the catheter, the toothed grip connector system comprising:
  - a recess extending longitudinally from a first end of the coupling system, the toothed grip connector system including an internal stem within the recess;
  - a gripping member extending radially about the internal stem, the gripping member including a plurality of teeth extending radially inward, the plurality of teeth configured to engage an outer surface of the end portion of the catheter to prevent longitudinal movement in at least a first direction following insertion of the end portion of the catheter into the recess; and
  - a sealing member configured to impinge on the outer surface of the end portion of the catheter to provide a seal between the end portion of the catheter and the internal stem; and
- a disengagement tool, a portion of the disengagement tool configured to extend into the recess between the outer surface of the end portion of the catheter and a tooth of the plurality of teeth, to disengage the plurality of teeth from the catheter and allow the catheter to be withdrawn along the first direction.

2. The coupling system according to claim 1, further including a male-end quick connector disposed at a second end of the coupling system, configured to engage a female-end quick connector coupled to the access port.

3. The coupling system according to claim 1, wherein the plurality of teeth is angled toward a second end of the coupling system, opposite the first end of the coupling system.

4. The coupling system according to claim 1, wherein one of the gripping member or the sealing member is retained within a groove in a wall defining the recess, the groove extending annularly about the internal stem.

5. The coupling system according to claim 1, wherein a protrusion extends radially inward from a wall defining the recess and is configured to abut against one of the gripping member or the sealing member to inhibit longitudinal movement of the gripping member or the sealing member in at least the first direction.

6. The coupling system according to claim 1, wherein the sealing member includes material selected from a silicone, a polymer, an elastomer, or a rubber material that exhibits fluid tight properties.

7. The coupling system according to claim 1, wherein the sealing member is located proximate a second end of the coupling system and the gripping member is located proximate the first end of the coupling system.

* * * * *